United States Patent [19]
Rutner et al.

[11] 3,953,431
[45] Apr. 27, 1976

[54] DERIVATIVES OF DIGOXIGENIN

[75] Inventors: Herman Rutner, Hackensack, N.J.; Raul Rapun, Suffern; Nathan Lewin, New York, both of N.Y.

[73] Assignee: Becton, Dickinson & Company, Rutherford, N.J.

[22] Filed: Sept. 28, 1973

[21] Appl. No.: 401,816

Related U.S. Application Data

[62] Division of Ser. No. 146,545, May 24, 1971, Pat. No. 3,855,208.

[52] U.S. Cl. .................... 260/239.57; 260/112.5 R; 260/112 R; 424/241
[51] Int. Cl.² .......................................... C07J 19/00
[58] Field of Search .....................
/Machine Searched Steroids; 260/239.57

[56] References Cited
UNITED STATES PATENTS
3,655,643   4/1972   Lehmann et al. .............. 260/210.5
3,855,208   12/1974  Rutner et al. ................. 260/239.57

OTHER PUBLICATIONS
Oliver et al., Jour. Clinical Investigation, Vol. 47, pp. 1035–1042, (1968).

Primary Examiner—Elbert L. Roberts
Attorney, Agent, or Firm—Marn & Jangarathis

[57] ABSTRACT

Derivatives of digoxigenin which are either unlabeled or radioiodinated having the following structural formula:

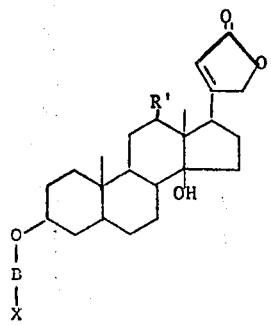

wherein R' is hydroxyl or acetoxy; B is succinyl, phthaloyl, maleyl or fumaryl, preferably succinyl, and X is hydroxyl or alkali metal salt thereof; a protein conjugate; a peptide conjugate; or an amino acid or amnio acid ester radical. The radiolabeled compounds are used in the radioimmunological assay of digoxin. The preferred compound is radioiodinated 3-succinyl digoxigenin-L-tyrosine.

9 Claims, No Drawings

DERIVATIVES OF DIGOXIGENIN

This is a division of Ser. No. 146,545, filed May 24, 1971.

FIELD OF THE INVENTION

This invention relates to new cardenolides and more particularly to new derivatives of digoxigenin and a method for their preparation. Still further this invention relates to the use of radiolabeled derivatives of digoxigenin in the radioimmunological assay of digoxin.

BACKGROUND OF THE INVENTION

Physicians have long sought better methods of judging proper therapeutic dosages and diagnosing digitalis toxicity. Recently, Smith, Bulter and Haber in an article entitled "Determination of Therapeutic and Toxic Serum Digoxin Concentrations by Radioimmunoassay", *New England Journal of Medicine*, Vol. 281, Pages 1212–1216 (1969) disclosed a method for determining serum digoxin concentrations by the use of tritiated digoxin, but the use of tritiated digoxin in the detection of serum digoxin of nonogram levels is subject to the inherent disadvantages of liquid scintillation counting which, in conjunction with the relatively low specific activity of commercially available tritiated digoxin, necessitates relatively large sample volumes and/or increased counting times in order to attain the requisite sensitivity and accuracy.

As a result of the limitations of tritiated cardenolide glycosides for radioimmunological assay, there is a need for other radiolabeled compounds, which can be effectively employed in the radioimmunological assay of digoxin in human serum.

SUMMARY OF THE INVENTION

Accordingly, an object of this invention is to provide new cardenolide derivatives.

A further object of this invention is to provide new derivatives of digoxigenin which are useful as or in the preparation of compounds for the radioimmunological assay of digoxin.

These and other objects of this invention should be more readily apparent from reading the following detailed description thereof.

In brief, the objects of this invention are accomplished by providing cardenolides represented by the following structural formula:

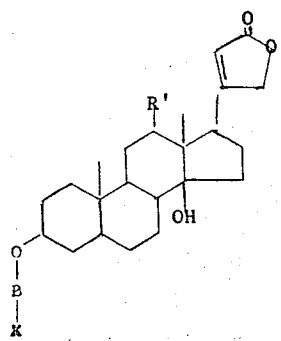

wherein
R' is —OH or —OCOCH₃;

B is a diacyl radical of a dicarboxylic acid in which the carboxy groups are substituted on adjacent carbon atoms, such as succinyl, maleyl, fumaryl or o-phthaloyl, preferably succinyl; and X is either:
a. —OH;
b. —OM wherein M is an alkali metal, preferably sodium;

c) 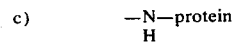

wherein the protein is generally either human serum albumin, insulin, lysozyme or bovine serum albumin, preferably human serum albumin or bovine serum albumin;

d) 

wherein the peptide preferably has no more than 20 units, and more preferably no more than 6 units, and at least one of the peptide units is formed from one of the following amino acids: L-tyrosine, 4-hydroxyphenylglycine, tryptophan, 5-hydroxy tryptophan and histidine and wherein one or more of the peptide units may be radiolabeled, preferably radioiodinated; or a. an amino acid radical wherein the amino acid radical is preferably one of the following:

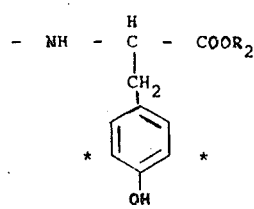

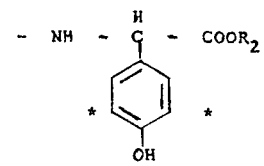

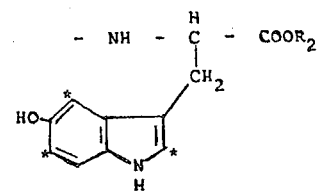

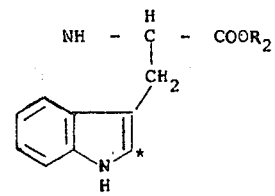

Step IV - Coupling

Digoxigenin-12-acetate-3-hemisuccinate

↓     - Protein
        - Peptide
        - Amino Acid
        or
        - Amino Acid ester 12-acetoxy-3-succinyl digoxigenin

- Protein
        or
        - Peptide
        or
        - Amino Acid
        or
        - Amino Acid ester

Step V - Hydrolyses

- Protein
        or
        - Peptide 3-succinyldigoxigenin or
        - Amino Acid
        - Amino Acid ester

Step VI - Radioiodination

- radioiodinated amino acid
        or 3-succinyldigoxigenin

- radioiodinated amino acid ester
        or
        - radioiodinated peptide

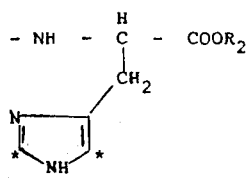

wherein $R_2$ is hydrogen or lower alkyl (up to six carbon atoms), the lower alkyl group preferably being methyl or ethyl and wherein the amino acid radical may be radiolabeled, preferably radioiodinated with one or two radioiodine atoms, with the probable positions thereof, if present, being represented by an asterisk. The preferred amino acid radicals are derived from L-tyrosine, histidine and 4-hydroxyphenylglycine, with L-tyrosine being most preferred.

The reaction scheme for preparing the digoxigenin derivatives of the present invention, using as a representative example those compounds in which moiety B of structural formula (1) is succinyl, is as follows:

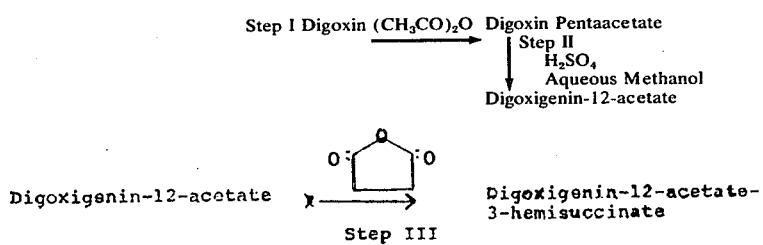

In the above reaction sequence, Steps I and II are known in the art, and the resulting product digoxigenin-12-acetate, is also known in the art, see for example Elsevier's Encyclopedia of Organic Chemistry, Vol. 14, Supplement 1969, Page 4562. The product of Step III, however, is a novel compound, as represented in hereinabove structural formula 1 wherein X is OH and R' is OCOCH₃.

The novel intermediate, digoxigenin-12-acetate-3-hemisuccinate (in structural formula (1) X is —OH and R' is OCOCH₃) may then be employed to produce the other novel compounds of the present invention, by the following reaction scheme:

The reaction products of Steps IV, V and VI are novel compounds. In the above reaction sequence, the amino acid or amino acid ester which is coupled to the digoxigenin-12-acetate-3-hemisuccinate is one of the following amino acids or their lower alkyl esters: L-tyrosine; 4-hydroxyphenylglycine; tryptophan; 5-hydroxytryptophan or histidine. The radioiodination is preferably effected with $^{125}$I, but it is to be understood that iodination could be effected with other iodine isotopes, such as $^{134}$I.

The 3-succinyl digoxigenin derivative of the present invention is prepared by hydrolysis of digoxigenin-12-acetate-3-hemisuccinate, as hereinafter described.

In the above reaction sequence, in Step III, the anhydrides of maleic acid and o-phthalic acid could be substituted for succinic anhydride to produce the compounds of the present invention in which moiety B of structural formula (1) is maleyl or o-phthaloyl. The compounds of the present invention in which moiety B of structural formula (1) is fumaryl are produced by isomerization, as known in the art, of compounds in which moiety B of structural formula (1) is maleyl.

DETAILED DESCRIPTION OF THE INVENTION

The reaction Steps I and II in the hereinabove described reaction scheme are known in the art, and the reaction product thereof, digoxigenin-12-acetate, is also known in the art. Accordingly, no detailed explanation of such reaction steps is deemed necessary for a full understanding of the invention. All temperatures are °C., unless otherwise indicated.

Step III

The novel compound, digoxigenin-12-acetate-3-hemisuccinate is produced by reacting digoxigenin- 12-acetate with succinic anhydride in the presence of a suitable inert solvent at a temperature which generally ranges from about 25°C. to about 150°C., preferably from about 80°C. to about 140°C. As representative examples of inert solvents, there may be mentioned: a hydrocarbon such as benzene, an ether such as diethyl ether, tetrahydrofuran or dioxane, a ketone such as acetone or methyl ethyl ketone, an ester such as ethyl acetate or butyl acetate, a halogenated hydrocarbon such as chloroform, methylene chloride, carbon tetrachloride, dichloroethane, and other solvents such as carbon disulfide, tetramethylurea, dimethylformamide, dimethylsulfoxide, preferably in combination with pyridine, collidine, quinoline, and other weak bases to prevent the formation of anhydro cardenolide derivatives. Pyridine, collidine and quinoline are also suitable by themselves.

The relative amounts of the succinic anhydride and digoxigenin-12-acetate are adjusted to provide the optimum results, and generally the relative amounts range from about stoichiometric proportions up to about 10 times stoichiometric proportions, and preferably from about 3 to about 5 times stoichiometric proportions. After evaporation in vacuo of most of the solvent, at a maximum temperature of 60°, preferably at 25°–40°, the residue is treated with water, and the excess succinic anhydride is allowed to hydrolyze in the presence of an alkali bicarbonate or comparable weak base. After removal of the unreacted starting material and neutral impurities by filtration and/or extraction with an immiscible solvent (e.g., dichloromethane, chloroform, benzene, ethyl acetate, etc.), the aqueous phase is acidified to yield nearly pure digoxigenin-12-acetate-3-hemisuccinate suitable for use in Step IV.

It is to be understood that maleic anhydride or phthaloyl anhydride could be used instead of succinic anhydride to produce digoxigenin-12-acetate-3-hemimaleate and digoxigenin-12-acetate-3-hemiphthalate, respectively. Digoxigenin-12-acetate-3-hemifumarate may be produced by isomerization, as known in the art, of digoxigenin-12-acetate-3-hemimaleate.

Step IV

Coupling of the amino acid ester with digoxigenin-12-acetate-3-hemisuccinate in Step IV may be performed by the procedure used for coupling an amino acid ester to 3-o-succinyl digitoxigenin as described by Oliver et al. *J. Chemical Investig.*, Vol. 47 1035–1042 (1968) using isobutyl chloroformate for mixed anhydride formation. Alternatively, pivaloyl chloride or N-ethoxycarbonyl-2-ethoxy-1,2-dihydroquinoline (EEDQ) serves the same purpose. The mixed anhydride can be generated under anhydrous conditions in an inert solvent such as dichloromethane, chloroform, ethyl acetate, dioxane, tetrahydrofurane, monoglyme, diglyme, etc., at a temperature ranging from −10° to 25°, preferably at −5° to 10°, in the presence of one equivalent of an organic base, e.g., triethylamine, tri-n-butylamine, tri-n-octylamine, N-methylmorpholine, etc. Coupling with the appropriate amino acid alkyl ester can be conducted in aqueous solvents e.g., 50% aqueous dioxane, as indicated in prior art or, preferably in the afore-mentioned anhydrous solvents in the presence of an additional equivalent of base.

Alternatively, EEDQ may be utilized for coupling both reactants, admixed in the afore-mentioned anhydrous solvents, at a temperature of 5° to 30° for several hours or until reaction is complete.

As a further alternative a free amino acid instead of an alkyl amino acid ester may be linked to the digoxigenin-12-acetate-3-hemisuccinate by the use of the hereinabove described anhydrous conditions.

Isolation of the desired neutral coupling product involves removal of basic and acidic impurities, including unreacted starting material by contacting the solution of the reaction mixture in an immiscible solvent, e.g., dichloromethane, chloroform, benzene, ethyl acetate, etc., with dilute aqueous mineral acid and with dilute aqueous alkali bicarbonate, alkali carbonate or alkali hydroxide, respectively. Neutral impurities, primarily N-acyl-amino acid esters, are subsequently removed on the basis of molecular size via gel filtration and/or on the basis of polarity via silica gel chromatography and/or preparative thin layer chromatography. Removal of neutral impurities is desirable, but not essential prior to hydrolysis in Step V.

The protein and peptide derivates of the present invention may also be produced from the novel intermediate of the present invention, digoxigenin-12-acetate-3-hemisuccinate by the procedures described by Oliver et al. *J. Chemical Investig*, Vol. 47, Pages 1035–1042 for coupling human serum albumin and bovine serum albumin to 3-0-succinyl digitoxigenin (SDG). In the present invention, digoxigenin-12-acetate-3-hemisuccinate is used instead of SDG. The peptide (the term peptide includes polypeptides) used for preparing the peptide derivatives of the present invention is one that includes one or more moieties suitable for iodination, such as 4-hydroxyglycine, tyrosine, 5-hydroxytryptophan, tryptophan, histidine, and as representative examples of such peptides, there may be mentioned: L-Tyrosyl-L-Lysine, L-Tyrosyl-L-Glutamic acid, L-Tyrosyl-L-Tyrosine, L-Tryptophyl-L-Glutamic Acid, L-Tryptophyl Glycine, L-Tryptophyl-L-Tyrosine, L-Tryptophyl-L-Lysine, L-Leucyl-L-Tryptophyl-L-Methionyl-L-Arginyl-L-Phenylalanyl-L-Alanine, L-Histidyl-L-Alanine, L-Histidyl-L-Glutamic Acid, L-Histidyl-L-Tyrosine and Gramicidin. It is to be understood that the hereinabove described peptides may be linked to the digoxigenin-12-acetate-3-hemisuccinate, by the method particularly described by Oliver et al. with respect to human serum albumin and bovine serum albumin. Alternatively, the low molecular weight peptides may be linked to the digoxigenin-12-acetate-3-hemisuccinate by the anhydrous method hereinabove described for linking an amino acid or amino acid ester to digoxigenin-12-acetate-3-hemisuccinate.

It is to be understood that the hereinabove description of the processing conditions for Step IV are also applicable to the maleate and phthalate derivatives of the present invention.

Step V

The reaction Step V involves selective hydrolysis of the 12 acetate group of the cardenolide or the alkyl group of the amino acid moiety ($R_2$ of structural formula (1)) or both by bringing the product of Step IV in contact with an excess of base ranging from about 5 to about 50 equivalents, preferably from about 10 to about 20 equivalents, in the presence of water and/or an inert solvent. The bases which may be employed in this step are exemplified by: triethylamine, sodium carbonate, potassium carbonate, sodium hydrogen carbonate, potassium hydrogen carbonate, ammonia or the like. Especially preferred are alkali metal carbonate, alkali metal hydrogen carbonate and ammonia. A preferred inert solvent of this step is a water-miscible solvent, for instance alcohols such as methanol, ethanol, propanol, sec-butanol, tert-butanol, amyl alcohol, etc., ketones such as acetone, methyl ethyl ketone, etc., ethers such as diethyl ether, dioxan or tetrahydrofuran and the other solvents such as dimethyl formamide, dimethylsulfoxide and the like. They may be mixed with each other so as to dissolve the reagent or the starting material. Hydrolysis of this step usually requires water, but in some cases the reaction may proceed via hydrolysis or exchange reaction of carbonate residue and hydrogen atom of the solvent or reagent.

The hydrolysis is effected at a temperature from about 5°C. to about 50°C., preferably from about 20° to about 25° for a period of 5 to 20 days for alkali metal bicarbonates or for 3 to 48 hours for alkali carbonates and bases of comparable basicity. Limited action of alkali bicarbonates on 3-succinyl-digoxigenin-L-tyrosine methyl ester permits isolation of the two partial hydrolysis products. 3-succinyl-12-acetoxy digoxigenin-L-tyrosine ($R^1$ = $OCOCH_3$, X = tyrosine, $R_2$ = H) and 3-succinyl digoxigenin-L-tyrosine methyl ester ($R^1$ — OH, X = tyrosine, $R_2$ = $CH_3$) in approximately equal amounts. The former compound is also obtained directly from digoxigenin-12-acetate-3-succinate pivaloyl mixed anhydride and L-tyrosine in anhydrous pyridine in the presence of one equivalent of base.

Similarly, selective hydrolysis of digoxigenin-12-acetate-3-hemisuccinate with a twenty fold excess of aqueous alkali carbonate results in the formation of ligoxigenin-3-succinate (in structural formula (1) R' is —OH and X is —OH), a novel derivative of digoxigenin capable of forming water-soluble alkali metal salts.

Similarly, treatment of peptide or protein conjugates of digoxigenin-12-acetate-3-hemisuccinate prepared analogous to the hereinabove referred to method of Oliver et al. with aqueous alkali bicarbonates or alkali carbonates at a temperature of 5° to 25° for periods ranging from several days to several hours, respectively, effects selective removal of the 12-acetoxy group to provide the novel derivatives of the present invention in which in structural formula (1) R' is OH and X is the moieties represented by (c) and (d).

The hydrolysis product is recovered by a sequence of steps comprising neutralization, removal of neutral impurities, precipitation by acidification in the examples where X is an amino acid or small peptide moiety, preparative thin layer chromatography and/or gel filtration.

For derivatives containing side chains of higher molecular weight such as those containing polypeptides or proteins, dialysis where permissible, or gel filtration is the method of the choice. In all cases, complete removal of iodinatable impurities is effected prior to iodination.

It is to be understood that the hereinabove description of the processing conditions for Step V are equally applicable to the maleyl and phthaloyl derivatives of the invention.

Step VI

The radioiodinated derivatives may be prepared by one of the following methods:

1. Chloramine T Method of Hunter-Greenwood, W. M. Hunter, F. C. Greenwood, Nature 194, 495 (1962);

2. Iodine Monochloride Method, M. Ceska, F. Grossmuller, U. Lundkvist, Acta Endocrinologia 64, 111—125 (1970);

3. Isotopic Exchange Method, R. E. Counsell, V. V. Ranade, P. Pocha, R. E. Willette, W. Diquilio, J. Pharmaceut, Sciences 57, 1657 (1968); and 4. Electrolytic Iodination, P. Pennisi, U. Rosa, J. Nuclear Biol. and Medicine 13, 64 (1964).

Water-soluble substrates, e.g., those bearing solubilizing carboxylic functions or peptide groups in moiety X, are iodinated in aqueous media. Iodination of lipophilic substrates such as alkyl ester ($R_2$ = alkyl in formula (1)) requires the use of inert solvents or aqueous solvents comprising water and water miscible solvents such as methanol, ethanol, dioxane, tetrahydrofurane, dimethyl formamide, dimethyl sulfoxide, etc.

After iodination, unreacted labeled iodide is removed by methods in the art, e.g., via absorption on an ion exchange resin. The co-absorbed iodinated cardenolides may then be eluted selectively with an appropriate organic solvent. Polypeptide or protein conjugates are purified by dialysis, where permissible, followed by gel filtration or electrophoresis. The extent of diiodination, where possible, is controllable by varying the substrate to iodine ratio over the range of 1:1 to 100:1. As an example, for X = tyrosine, a ratio of 2.5:1 yields 15–20% diiodinated antigen compared to 5–7% at a ratio of 25:1. The singly and doubly labeled derivatives of low molecular weight can be readily resolved via preparative TLC or via silica gel chromatography to yield both components in > 95% purity.

It is to be understood that the hereinabove described processing conditions of Step VI are equally applicable to the maleyl and phthaloyl derivatives of the present invention.

The following examples further illustrate the invention, but it is to be understood that the scope of the invention is not to be limited thereby. Unless otherwise specified, all parts are by weight and all temperatures are °C.

EXAMPLE I

A. A mixture of 1.37 g. digoxigenin-12-acetate, 1.27 g succinic anhydride and 15 cc pyridine is refluxed for seven hours. The reaction mixture is quenched with aqueous sodium bicarbonate solution and concentrated to remove pyridine. Acidification yields 1.55 g crude digoxigenin-12-acetate-3-hemisuccinate.

Purification by preparative thin layer chromatography and re-precipitation from water affords pure digoxigenin-12-acetate-3-hemisuccinate, melting point 135°–140°, $[\alpha]_D^{23}$ + 42° (c = 0.265, methanol), log $\epsilon$ 4.21 at 217 m$\mu$ (methanol).

The above procedure is employed to produce digoxigenin-12-acetate-3-hemimaleate and digoxigenin-12-acetate-3-hemiphthalate by substituting maleic anhydride and 0-phthalic anhydride, respectively, for succinic anhydride.

B. A solution of 230 mg digoxigenin-12-acetate-3-hemisuccinate in 25 cc water containing 1.20 g potassium carbonate is kept at 25° for 46 hours. The mixture is acidified with dilute hydrochloric acid to precipitate the crude product.

Purification by thin layer chromatography and by crystallization from aqueous acetone yields 74 mg digoxigenin-3-hemisuccinate, melting point 211°–213° $[\alpha]_D^{23}$ + 20° (c = 0.356, methanol), log $\epsilon$ 4.20 at 218 m$\mu$ (methanol).

Digoxigenin-3-hemimaleate and digoxigenin-3-hemiphthalate are also prepared by this procedure by using as the starting material digoxigenin-12-acetate-3-hemimaleate and digoxigenin-12-acetate-3-hemiphthalate, respectively.

EXAMPLE II

A. A mixture of 216 mg digoxigenin-12-acetate-3-hemisuccinate, 4 cc dichloromethane, 0.04 cc triethylamine, and 0.052 cc pivaloyl chloride is stirred at 20° for 15 minutes and chilled to −10° prior to addition of a chilled (−10°) solution of 88 mg L-tyrosine methyl ester hydrochloride, 0.072 cc tri-n-butylamine and 2 cc pyridine. The mixture is stirred for 10 minutes at −10° to −5° and at ambient temperature for one hour. The mixture is diluted with water, acidified with 6 N hydrochloric acid and extracted with dichloromethane. The extract is washed several times with 1% aqueous sodium bicarbonate and water, dried and evaporated to leave a gummy residue which is purified by thin layer chromatography. Pure 12-acetoxy-3-succinyl digoxigenin-L-tyrosine methyl ester is obtained as a colorless gum, $[\alpha]_D^{23} + 42°$ (c = 0.293, methanol); log ε 4.42 at 222 mμ, 3.34 at 276 mμ (methanol) and 4.32 at 221 mμ, 3.43 at 294 mμ (0.1 N NaOH).

The above procedure is repeated using the methyl and ethyl esters of histidine and 4-hydroxy phenylglycine, and the ethyl ester of L-tyrosine to produce the corresponding amino acid ester derivatives.

B. A mixture of 25 mg crude 12-acetoxy-3-succinyl digoxigenin-L-tyrosine methyl ester, 2.5 cc methanol and 2.5 cc water containing 100 mg potassium carbonate is kept at 25° for 3 hours. The mixture is acidified with dilute hydrochloric acid, evaporated to remove methanol and extracted with ethyl acetate. The extract is washed with water, dried and evaporated to dryness. The residue is purified by thin layer chromatography to yield 4 mg 3-succinyl digoxigenin-L-tyrosine, melting point 165°–175°, $[\alpha]_D + 45°$ (cc = 0.245, methanol), log ε 4.40 at 222 mμ, 3.29 at 276 mμ (methanol); 4.34 at 220 mμ, 3.39 at 294 mμ (0.1 N NaOH).

The above procedure is also employed to hydrolize the other amino acid ester derivatives which are produced by the procedure of Example II A to produce the corresponding amino acid derivatives.

EXAMPLE III

A. Digoxigenin-12-acetate-3-hemisuccinate was coupled to bovine serum albumin by the method of Oliver et al., J. Clinical Investig. 47, 1035–1042 (1968). The resultant acetylated conjugate contains 34 molecules of digoxigenin per molecular of bovine serum albumin as determined by the sulfuric acid method of Butler and Chen, [V. P. Butler, Jr., and J. P. Chen, Proc. Nat. Acad. Sci. 47, 71–78 (1967)].

B. Digoxigenin-12-acetate-3-succinate-BSA conjugate (81 mg), 165 mg potassium carbonate and 3 cc water is kept at 23° for 3 hours. The mixture is neutralized with 0.075 cc acetic acid and dialyzed for four days at 5°. The dialysate is centrifuged and the supernatant layer is lyophilized to yield 65 mg digoxigenin-3-succinyl-bovine serum conjugate containing 28 molecules of digoxigenin per molecule of BSA.

EXAMPLE IV

A. Following the procedure described in Example II B, but substituting potassium bicarbonate for potassium carbonate and allowing the reaction to proceed for four days permits isolation of both 12-acetoxy-3-succinyl digoxigenin-L-tyrosine and 3-succinyl-digoxigenin-L-tyrosine methyl ester.

The above procedure is also employed to hydrolyze the other amino acid ester derivatives which are produced by the procedure of Example II A to produce the corresponding derivatives.

B. Addition of the mixed pivalic acid and digoxigenin-12-acetate-3-hemisuccinate (prepared as in Example II A from 79 mg digoxigenin-12-acetate-3-hemisuccinate) to a suspension of 27 mg L-tyrosine, 0.038 cc tri-n-butylamine and 5 cc pyridine, stirring for 16 hours at 25° and isolation as in Example II B affords 12-acetyl-3-succinyl digoxigenin-L-tyrosine identical to the material in Example IV A.

The procedure of Example IV B is repeated with histidine and 4-hydroxyphenylglycine instead of L-tyrosine to produce the corresponding amino acid derivatives.

EXAMPLE V

A. Iodination of 10 g 3-succinyl digoxigenin-L-tyrosine produced by the procedure of Example II B with 9 mc $^{125}$I is effected at pH 7.4 by the method of Hunter and Greenwood at a substrate to iodine ratio of 2.5 to 1. Unreacted iodide is removed by passage through a quarternary amine anion exchange resin in the chloride form. The co-absorbed product is eluted and contains 4.06 mc $^{125}$I in the two iodination products, 3-succinyl-digoxigenin-(3'-iodo-L-tyrosine-$^{125}$I) and 3-succinyl digoxigenin-(3',5'-diiodo-L-tyrosine-$^{125}$I$_2$) which are formed in the ratio of 6 to 1. Separation of both components in radio-chemical purity of greater than 95% is achieved by thin layer chromatography.

B. Iodination of 60 g 3-succinyl digitoxigenin-L-tyrosine with 6 mc $^{125}$I at a substrate to iodine ratio of 25:1 yields a total of 4.13 mc $^{125}$I in the mono and diiodination products obtained in the ratio of 13 to 1.

C. The 3-succinyl-digoxigenin amino acid esters which are produced in Example IV A are radioiodinated by the procedure disclosed by Oliver et al.

The procedure of Example V A is repeated with the other amino acid derivatives (3-succinyl digoxigenin-histidine; and 3-succinyl digoxigenin-4-hydroxyphenylglycine) to produce radio-iodinated derivatives.

EXAMPLE VI

A. A mixture of 216 mg digoxigenin-12-acetate-3-hemisuccinate, 4 cc dichloromethane, 0.04 c; triethylamine, and 0.052 cc pivaloyl chloride is stirred at 20° for 15 minutes and chilled to −10° prior to addition of a chilled (−10°) solution of 88 mg of the peptide L-tyrosyl-L-lysine, 0.072 cc tri-n-butylamine and 2 cc dimethylformamide. The mixture is stirred for 10 minutes at −10° to −5° and at ambient temperture for one hour. The mixture is diluted with water, acidified with 6 N hydrochloric acid and extracted with ethyl acetate. The extract is washed several times with 1% aqueous sodium bicarbonate and water, dried and evaporated to leave a gummy residue which is purified by thin layer chromatography to produce 12-acetoxy-3-succinyl digoxigenin-L-tyrosyl-L-lysine.

B. A mixture of 25 mg of the product of Example VI A, 2.5 cc methanol and 2.5 cc water containing 100 mg potassium bicarbonate is kept at 25° for 3–5 days. The mixture is acidified with dilute hydrochloric acid, evaporated to remove methanol and extracted with ethyl acetate. The extract is washed with water, dried and evaporated to dryness. The residue is purified by thin layer chromatography to yield 3-succinyl digoxigenin-L-tyrosyl-L-lysine.

C. The product of Example VI B is radioiodinated by the procedure described by Oliver et al. in the hereinabove referenced article, to produce radioiodinated 3-succinyl digoxigenin-L-tyrosyl-L-lysine.

D. The product of Example VI A is also radioiodinated by the procedure described by Oliver et al. to produce radioiodinated 12-acetoxy-3-succinyl digoxigenin-L-tyrosyl-L-lysine.

The procedures of Examples VI A-C are repeated with the following peptides: L-Tyrosyl-L-Glutamic Acid, L-Tyrosyl-L-Tyrosine, L-Tryptophyl-L-Glutamic Acid, L-Tryptophyl Glycine, L-Tryptophyl-L-Tyrosine, L-Tryptophyl-L-Lysine, L-Leucyl-L-Tryptophyl-L-Methionyl-L-Arginyl-L-Phenylalanyl-L-Alanine, L-Histidyl-L-Alanine, L-Histidyl-L-Glutamic Acid, L-Histidyl-L-Tyrosine, and Gramicidin.

It is to be understood that the procedures of Examples II, IV, V and VI are also applicable to the hemimaleate and hemiphthalate derivatives produced by the procedure of Example I A. The fumaryl derivatives of the present invention are produced from the maleyl derivatives by the isomerization procedures known in the art for isomerizing maleic acid to fumaric acid.

The radioiodinated derivatives of the present invention; i.e., the radioiodinated compounds of structural formula (1) wherein R' is —OH or —OCOCH$_3$ and X is one of the radicals designated as (d) or (e); may be used as the labeled antigen in the radioimmunological assay of digoxin. A radioimmunological assay procedure which may be employed is one which is a slight modification of the radioimmunological assay disclosed by Smith et al. *New England Journal of Medicine*, Vol. 281, Pages 1212–16 (March 27, 1969) for tritium labeled digoxin as follows:

To 1 ml of serum in disposable plastic test tubes, 12 by 75 mm (Falcon Plastics, Los Angeles, California), is added, with thorough mixing, 3 ng of a radioiodinated derivative of the present invention. Antidigoxin antibody is then added in an amount sufficient to produce 37 to 50 percent binding of the radioiodinated derivative in the absence of unlabeled drug, and the mixture incubated at 25°C. for 1 hour. Competition between the radioiodinated compound and unlabeled digoxin for antibody binding sites determines the amount of the radioiodinated compound-antibody complex present at equilibrium. Separation of bound from free radioiodinated compound is achieved by the dextran-coated charcoal technique of Herbert et al., *J. Chem. Endocr.* Vol. 25, 1375–1384 (1965) resulting in selective binding of free labeled and unlabeled compound to the coated charcoal, which was then separated by centrifugation. The supernatant phase was decanted and counted in a gamma counter.

The immunogens of the present invention; i.e., the compounds of structural formula (1) wherein R' is —OH and X is the protein conjugate designated as (c), may be employed to produce anti-digoxin antibody by the methods presently known in the art for producing anti-digitoxigenin antibodies from the protein conjugates of 3-succinyl digitoxigenin, as disclosed in the hereinabove referred to article by Oliver et al.

The compound digoxigenin-3-succinate in the form of its alkali metal salt, in particular sodium, may be employed for the same pharmacological purposes and in the same amounts as digoxigenin, except that the sodium salt of digoxigenin-3-succinate is water soluble, whereby the compound may be employed as an injectable water solution. The corresponding fumarate, maleate and o-phthalate derivatives may be employed in a similar manner.

The radioiodinated derivatives of the present invention are particularly useful for the radioimmunological assay of digoxin in human serum. Although radioiodinated derivatives of digitoxigenin are known in the art; e.g., the radioiodinated 3-succinyl-digitoxigenin-L-tyrosine methyl ester, as reported in *The Journal of Clinical Investigation*, Vol. 47, Pages 1035–1042 (1968), such derivatives can not be employed for measuring serum digoxin levels due to unfavorable immunological cross-reactivity.

The radioiodinated cardenolide derivatives of the present invention are an improvement over the tritiated digoxin presently employed in the art for the radioimmunological assay of digoxin for the following reasons:

1. An inexpensive well-counter may be used as compared to the costly and complex liquid scintillation counters required for the tritiated compound.

2. Liquid scintillation fluids and special vials are not needed.

3. No internal or external standardizations are needed as in the case of the tritiated digoxin.

4. Counting efficiencies are higher, particularly in aqueous media. In addition, the radioiodinated derivatives of the present invention in which the amino acid moiety is in acid form, instead of an ester (in structural formula (1) R$_2$ is H) significantly increases the polarity, solubility and hydrophilicity of the compound whereby such derivatives are water-soluble at physiological pH values; can be iodinated in aqueous media; possess a side chain more nearly comparable in polarity to the tri-digitoxose moiety of natural cardenolides; exhibit superior binding to antibodies; and shown a lesser tendency toward adsorption on lipophilic surfaces, e.g., plastic test tubes.

Numerous modifications and variations of the present invention are possible in light of the above teachings and, accordingly, within the scope of the appended claims the invention may be practiced in a manner other than as particularly described.

What is claimed is:

1. A composition of matter comprising a compound having the following structural formula:

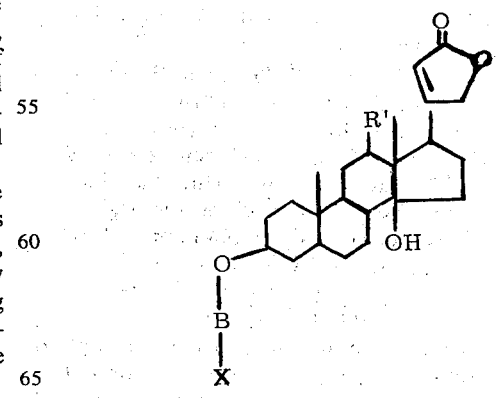

wherein

R' is selected from the group consisting of —OH and OCOCH₃;
B is selected from the group consisting of succinyl, maleyl, fumaryl and o-phthaloyl; and
X is selected from the group consisting of —OH and OM wherein M is an alkali metal.

2. The compound of claim 1 wherein B is succinyl.
3. The compound of claim 2 wherein X is OH.
4. The compound of claim 3 wherein R' is —OH.
5. The compound of claim 3 wherein R' is —OCOCH₃.
6. The compound of claim 2 wherein X is OM.
7. The compound of claim 6 wherein M is sodium.
8. The compound of claim 7 wherein R' is —OH.
9. The compound of claim 7 wherein R' is —OCOCH₃.

* * * * *

UNITED STATES PATENT OFFICE
CERTIFICATE OF CORRECTION

Patent No. 3,953,431              Dated April 27, 1976

Inventor(s)    Herman Rutner et al.

It is certified that error appears in the above-identified patent and that said Letters Patent are hereby corrected as shown below:

Column 2, line 30, delete "a.", and insert -- e) --.

Column 7, line 52, "molecular" should be -- molecule --.

Column 10, line 49, after "0.04c", there should be another -- c --.

line 57, "N" should be underlined.

Signed and Sealed this

Nineteenth Day of October 1976

[SEAL]

*Attest:*

RUTH C. MASON
*Attesting Officer*

C. MARSHALL DANN
*Commissioner of Patents and Trademarks*